United States Patent [19]

Muhr et al.

[11] Patent Number: 5,616,723

[45] Date of Patent: Apr. 1, 1997

[54] PROCESS FOR THE PREPARATION OF 3-AMINO-5-METHYLPYRAZOLE

[75] Inventors: Jürgen Muhr, Alfter; Marcel Feld, Köln, both of Germany

[73] Assignee: Hüls Aktiengesellschaft, Marl, Germany

[21] Appl. No.: 611,282

[22] Filed: Mar. 6, 1996

Related U.S. Application Data

[63] Continuation of Ser. No. 224,476, Apr. 7, 1994, abandoned.

[30] Foreign Application Priority Data

May 5, 1993 [DE] Germany .......................... 43 14 851.4

[51] Int. Cl.⁶ .................................................. C07D 231/12
[52] U.S. Cl. ................................................... 548/371.4
[58] Field of Search .......................................... 548/371.4

[56] References Cited

FOREIGN PATENT DOCUMENTS

| | | | |
|---|---|---|---|
| 650448 | 10/1962 | Canada | 548/371.4 |
| 680333 | 2/1964 | Canada | 548/371.4 |
| 596286 | 5/1994 | European Pat. Off. | 548/371.4 |
| 2643640 | 4/1977 | Germany | 548/371.4 |

*Primary Examiner*—Jacqueline Haley
*Attorney, Agent, or Firm*—Felfe & Lynch

[57] ABSTRACT

3-Amino-5-methylpyrazole is prepared by reaction of cyanoacetone or an alkali metal salt thereof with hydrazine, a hydrazinium salt, or hydrazine hydrate.

8 Claims, No Drawings

PROCESS FOR THE PREPARATION OF 3-AMINO-5-METHYLPYRAZOLE

This application is a continuation of application, Ser. No. 08/224,476, filed Apr. 7, 1994, now abandoned.

FIELD OF THE INVENTION

This invention relates to a novel method for the preparation of 3-amino-5-methylpyrazole and salts thereof, which comprises reacting cyanoacetone or an alkali metal salt thereof with a hydrazinium salt, hydrazine hydrate or free hydrazine. 3-Amino-5-methylpyrazole is useful as a precursor for magenta couplers, i.e. fuchsin, in photographic materials, and as an intermediate in the synthesis of pharmaceuticals.

BACKGROUND OF THE INVENTION

Prior art syntheses of 3-amino-5-methylpyrazole start from hydrazine hydrate and 3-aminocrotononitrile (Japanese Patent Application 63239272; Derwent OD-326015/88) or from 2-iminobutyronitrile (Soviet Patent No. 1413106; Derwent OD-038663/89). The starting materials for these known processes are difficult to obtain or chemically unstable, and the methods themselves are multistage, complicated syntheses with insufficient yields.

OBJECTS OF THE INVENTION

It is an object of the present invention to provide a process for the preparation of 3-amino-5-methylpyrazole with high yields and purity, which is simple to carry out and starts from readily available starting materials, thereby avoiding all of the shortcomings of the prior art processes.

Other objects and advantages of the present invention will become apparent as the description thereof proceeds.

DESCRIPTION OF THE INVENTION

The above object is achieved in accordance with the present invention by a process which comprises reacting an alkali metal salt of cyanoacetone with hydrazine or a derivative thereof while splitting off water and forming 3-amino-5-methylpyrazole and an alkali metal salt, or by forming cyanoacetone in situ and cyclizing it into 3-amino-5-methylpyrazole in one step.

The use of the sufficiently stable alkali metal salt of cyanoacetone or even cyanoacetone itself is preferred, especially when it is formed in situ during the reaction. Cyanoacetone (acetoacetonitrile) of the formula $H_3C-CO-CH_2-CN$ and alkali metal salts thereof are accessible by the Claisen method, i.e., by cleavage of 5-methylisoxazole (Beilstein $H_3$, 659).

The condensation of an alkali metal salt of cyanoacetone, especially the sodium or potassium salt with a hydrazinium salt such as hydrazinium hydrochloride, hydrazine or hydrazine hydrate is preferably carried out in a homogeneous or a two-phase solvent mixture. Suitable solvents for this purpose are, surprisingly, particularly water and also organic solvents such as ethanol, ether or hydrocarbons of 2 to 8 carbon atoms, as well as alkyl-substituted aromatics, especially toluene or xylene, optionally together with water.

Preferably, a solution or suspension of one of the reactants is added at the reaction temperature to a solution or suspension of the other reactant. The reactants can also be charged into the reaction vessel together in solution or suspension. All or some of the water can be removed by distillation or azeotropically by means of an entrainment agent during or after the reaction. Metering of the hydrazine reactant into the heated reaction mixture is advantageous for safety reasons. The process may also be performed in continuous fashion.

The reaction is carried out at a temperature between 10 and 200° C., preferably at the boiling point of the solvent which is used, at atmospheric pressure or optionally at a pressure up to 10 bar. If the reaction is carried out in an aqueous medium, a temperature of 30° to 100° C. is preferred. If the reaction is performed with aqueous hydrazinium monohydrochloride, for instance in the form of a solution, the pH is preferably adjusted to 1 to 2 with an acid, such as hydrochloric acid. Amounts of up to 1 mol-% are sufficient for this purpose.

Suitable entrainment agents for the azeotropic distillation are alkylbenzenes such as xylene or toluene, which may already be present during the condensation. The addition of water-binding auxiliary substances before, during or after the reaction is possible, as is the reaction in an anhydrous medium.

Since cyanoacetone tends to polymerize during storage, it should be prepared immediately prior to or at the beginning of the reaction, for instance by hydrolysis of an alkali metal salt of cyanoacetone in the presence of a hydrazinium salt, hydrazine or an aqueous solution of hydrazine hydrate by addition of an acid. The alkali metal salt of cyanoacetone can be charged into the reaction vessel together with hydrazine hydrate, for example, and the reaction may be initiated by metering in an acid such as hydrochloric acid. The reaction mixture may then be worked up in analogy to the work up of the reaction mixture formed by the preparation from an alkali metal salt of cyanoacetone and a hydrazine salt.

An alkali metal salt, usually sodium chloride, is formed in addition to 3-amino-5-methylpyrazole. If the reaction is carried out in a hydrophobic solvent such as toluene, this alkali metal salt may, even after removal of the water, form an unfilterable suspension in the low melting point 3-amino-5-methylpyrazole.

The isolation of the end product may, however, be readily achieved by separating the water, crystallizing the alkali metal salt in readily filterable form by adding a low molecular weight alkanol or ketone, preferably methanol or especially ethanol, in the presence of or after distilling off any entrainment agent which may have been used, and separating the product by a conventional solid/liquid separation procedure. The condensation reaction according to the present invention and the removal of the water of reaction by distillation may also be directly carried out with the solvents used for precipitation of the alkali metal salt, preferably with a branched or straight chain alkanol of 1 to 5 carbon atoms, especially preferably with ethanol. After separating the alkali metal salt, the desired end product may be isolated from the filtrate, preferably by distillation. However, it is also possible to convert the 3-amino-5-methylpyrazole into the corresponding salt by adding a mineral or carboxylic acid to the filtrate, and to isolate it in this form.

The following examples illustrate the present invention and will enable others skilled in the art to understand it more completely. It should be understood, however, that the invention is not limited solely to the particular examples given below.

EXAMPLE 1

1 Mol of hydrazinium monohydrochloride in the form of a 40% by weight aqueous solution in admixture with 200 ml of toluene were heated to reflux, and then 1 mol of sodium cyanoacetone in the form of a 30% by weight aqueous solution was added to the refluxing mixture over a period of 2½ hours. After the residual amount of water had been removed, toluene was distilled off and sodium chloride was precipitated by adding ethanol. After filtering off the sodium chloride, the filtrate was concentrated and purified by vacuum distillation, yielding 72 g (74% of theory) of 99% pure 3-amino-5-methylpyrazole having a boiling point (2 mm) of 128° C.

EXAMPLE 2

The pH of a 40% by weight aqueous solution containing 1.43 mols of hydrazinium monohydrochloride was adjusted to between 1 and 2 by adding catalytic amounts of concentrated hydrochloric acid. Equimolar amounts of sodium cyanoacetone were then metered into this solution at 30° C. over a period of 45 minutes. The reaction mixture was allowed to react for 4½ hours more, and then 650 ml of toluene were added to the reaction solution, and the water was removed by azeotropic distillation. Sodium chloride was precipitated from the solution by adding an equal volume of ethanol, the precipitate was filtered off, and the filtrate was concentrated and distilled in vacuo, yielding 100.6 g (71% of theory) of more than 98% pure 3-amino-5-methylpyrazole.

EXAMPLE 3

1 Mol of sodium cyanoacetone was added to 1 mol of a 40% by weight aqueous solution of hydrazinium monohydrochloride at 35° C. over a period of 2 hours. The mixture was allowed to react for 4½ hours more, and then 400 ml of toluene were added, the water was evaporated out of the solution, and then the toluene was distilled off. Sodium chloride was precipitated from the viscous residue by adding 200 ml ethanol and was filtered off, and the ethanol was removed from the filtrate in vacuo, yielding 99 g (88.6% of theory) of more than 89% pure 3-amino-5-methylpyrazole.

EXAMPLE 4

A suspension of 1 mol of sodium cyanoacetone and 1 mol of hydrazinium monohydrochloride in 300 ml of toluene was refluxed with a water separator until the amount of water which separated out remained constant. After cooling the reaction mixture, sodium chloride was precipitated by adding ethanol, the precipitate was filtered off, and the filtrate was worked up by distillation, yielding 71 g (72% of theory) of more than 98% pure 3-amino-5-methylpyrazole.

EXAMPLE 5

0.5 Mol of hydrochloric acid in the form of a 10% by weight aqueous solution was metered into a mixture of 52.5 g (0.5 mol) of sodium cyanoacetone and 0.45 mol of hydrazine hydrate in the form of a 30% by weight aqueous solution at 16° C. The temperature rose to 35° C., accompanied by the liberation of cyanoacetone, and was maintained at 35° C. for 4 hours more. The pH was then adjusted to 3 with concentrated hydrochloric acid. Thereafter toluene was added, the water was removed from the reaction mixture, and it was worked up as described in Example 1, yielding 36.8 g (72% of theory) of more than 95% pure 3-amino-5-methylpyrazole.

EXAMPLE 6

A suspension of 105.1 g (1 mol) of sodium cyanoacetone in toluene was heated to the boiling point, and 1 mol of a 40% by weight aqueous solution of hydrazinium monohydrochloride was added over a period of 2 hours while continuously removing water. After all of the water had been separated, the reaction mixture was worked up as described in Example 1, yielding 85.2 g (83.3% of theory) of more than 95% pure 3-amino-5-methylpyrazole.

While the present invention has been illustrated with the aid of certain specific embodiments thereof, it will be readily apparent to other skilled in the art that the invention is not limited to these particular embodiments, and that various changes and modifications may be made without departing from the spirit of the invention or the scope of the appended claims.

We claim:

1. A method of preparing 3-amino-5methylpyrazole which comprises reacting an alkali metal salt of cyanoacetone with hydrazine, a hydrazinium salt or hydrazinium hydrate.

2. The method of claim 1, which comprises reacting an alkali metal salt of cyanoacetone with a hydrazinium salt of a mineral acid.

3. The method of claim 1, which comprises performing the reaction in a solvent or in a suspension medium.

4. The method of claim 3, wherein the reaction is carried out in water, in an organic solvent, or in mixtures thereof.

5. The method according to claim 1, wherein any water formed by the reaction or added to the reaction mixture is removed during or after the reaction.

6. The method of claim 1, wherein the reaction is carried out in a temperature range of 10° to 200° C. at atmospheric pressure.

7. The method of claim 1, wherein the reaction is carried out in the temperature range of 20° to 60° C. at atmospheric pressure.

8. The method of claim 1, wherein the alkali metal salt of an acid radical introduced by the hydrazinium salt which is formed during the reaction is crystallized, any water formed by the reaction or introduced therein is separated, and the alkali metal salt is precipitated by addition of a low molecular weight alkanol or ketone, and the precipitated salt is separated by filtration.

* * * * *